(12) United States Patent
Park et al.

(10) Patent No.: US 11,013,920 B2
(45) Date of Patent: May 25, 2021

(54) APPARATUS FOR INDUCING ACTIVITY OF USER'S AUTONOMIC NERVOUS SYSTEM AND METHOD THEREOF

(71) Applicant: SEOUL NATIONAL UNIVERSITY R&DB FOUNDATION, Seoul (KR)

(72) Inventors: Kwang Suk Park, Seoul (KR); Hee Nam Yoon, Yongin-si (KR); Jee Hoon Kim, Gwacheon-si (KR); Sang Ho Choi, Anyang-si (KR); Hyun Bin Kwon, Daegu (KR); Yu Jin Lee, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 79 days.

(21) Appl. No.: 16/245,038

(22) Filed: Jan. 10, 2019

(65) Prior Publication Data

US 2019/0209843 A1    Jul. 11, 2019

(30) Foreign Application Priority Data

Jan. 11, 2018  (KR) .......................... 10-2018-0004055

(51) Int. Cl.
*A61N 1/00* (2006.01)
*A61N 1/36* (2006.01)
(Continued)

(52) U.S. Cl.
CPC .......... *A61N 1/36114* (2013.01); *A61B 5/024* (2013.01); *A61B 5/02405* (2013.01);
(Continued)

(58) Field of Classification Search
None
See application file for complete search history.

(56) References Cited

U.S. PATENT DOCUMENTS

| 2015/0158425 | A1* | 6/2015 | Han | G06K 9/00845 |
|---|---|---|---|---|
| | | | | 701/41 |
| 2016/0346501 | A1* | 12/2016 | Hooper | A61B 5/4836 |

FOREIGN PATENT DOCUMENTS

| JP | 2004-222818 A | 8/2004 |
|---|---|---|
| KR | 10-2014-0039287 A | 4/2010 |
| KR | 10-2012-0092249 A | 8/2012 |

OTHER PUBLICATIONS

Seo, Na Jin, et al. "Effect of Imperceptible Vibratory Noise Applied to Wrist Skin on Fingertip Touch Evoked Potentials—an EEG Study." Physiological Reports, vol. 3, No. 11, 2015, doi:10.14814/phy2.12624 (Year: 2015).*

* cited by examiner

*Primary Examiner* — Gary Jackson
*Assistant Examiner* — Anant A Gupta
(74) *Attorney, Agent, or Firm* — Husch Blackwell LLP

(57) ABSTRACT

A method for inducing an activity of a user's autonomic nervous system is provided. The method includes steps of: (a) on condition that each of the user's reference heart rate information corresponding to each of active states of the user's autonomic nervous system is obtained, an inducing device, if a specific active state of the autonomic nervous system is selected by the user, acquiring first reference heart rate information of the user corresponding to the specific active state of the autonomic nervous system; and (b) the inducing device supporting a first vibration stimulus with a first period corresponding to the first reference heart rate information to be applied to the user, to thereby allow the user's real-time average cardiac interval to be synchronized with the first vibration stimulus.

20 Claims, 6 Drawing Sheets

(51) Int. Cl.
*A61B 5/00* (2006.01)
*A61B 5/024* (2006.01)
*G16H 40/63* (2018.01)
*G16H 20/70* (2018.01)
*A61H 23/00* (2006.01)
*A61B 5/11* (2006.01)
*G16H 20/30* (2018.01)

(52) U.S. Cl.
CPC .......... *A61B 5/4035* (2013.01); *A61B 5/4836* (2013.01); *A61H 23/00* (2013.01); *G16H 20/70* (2018.01); *G16H 40/63* (2018.01); *A61B 5/1102* (2013.01); *G16H 20/30* (2018.01)

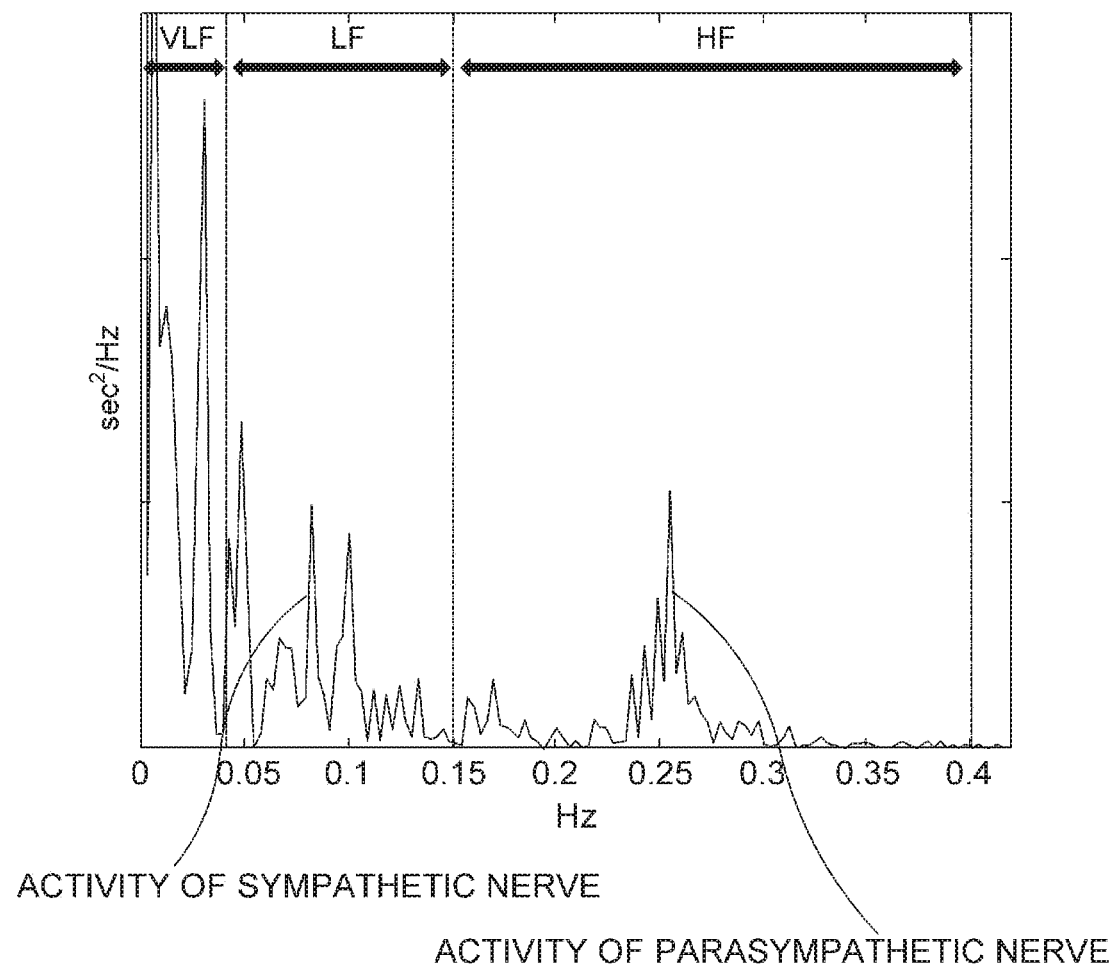

APPARATUS FOR INDUCING ACTIVITY OF USER'S AUTONOMIC NERVOUS SYSTEM AND METHOD THEREOF

FIELD OF THE DISCLOSURE

The present disclosure relates to a method for inducing an activity of a user's autonomic nervous system; and more particularly, to the method for inducing the activity of the user's autonomic nervous system, including steps of: (a) on condition that each of the user's reference heart rate information corresponding to each of active states of the user's autonomic nervous system is obtained, if a specific active state of the autonomic nervous system is selected by the user, acquiring first reference heart rate information of the user corresponding to the specific active state of the autonomic nervous system; and (b) supporting a first vibration stimulus with a first period corresponding to the first reference heart rate information to be applied to the user, to thereby allow the user's real-time average cardiac interval to be synchronized with the first vibration stimulus, and a inducing device using the same.

BACKGROUND OF THE DISCLOSURE

In general, the autonomic nervous system contributes to the maintenance of the homeostasis by performing the necessary control functions to maintain the internal environment of the human body through the antagonism of sympathetic and parasympathetic nerves.

The sympathetic nerve functions to cope with emergency situations such as tension, fear, and anger, and is related to an increase in heart rate and respiration, dilation of the pupil, suppression of gastrointestinal motility, and relaxation of the bladder.

The parasympathetic nerve is related to the stable state and performs functions such as energy conservation. It is associated with decrease of heart rate and respiration, increase of gastrointestinal motility, and bladder contraction.

In particular, the activities of the abnormal autonomic nervous system are closely related to stress, cardiovascular, nervous system and chronic diseases, and thus maintaining the balance of autonomic nervous system becomes the basis for restoring and maintaining a healthy life.

Accordingly, various methods for stably maintaining the balance of the activity of the autonomic nervous system have been proposed.

In particular, Korean Patent Laid-Open Publication No. 10-2012-0092249 discloses a sleep induction device capable of inducing a user's sleeping state by stimulating at least one of the five senses in consideration of the state of the user and its control method, and Korean Patent Laid-Open No. 10-2010-0039287 discloses a method for improving the concentration and the memory by adjusting the application of the optical flash and the pulse tone synchronized to a patient who needs at least one of concentration, memory, cognitive ability, and stress alleviation.

However, such a conventional apparatus and method maintains the user-desired sate through brain stimulation such as directly stimulating five senses according to the user's sleeping state or applying synchronized light flash and pulse tones within a preset frequency in an audiovisual assimilation for selective capability enhancement. However, since the stimulus is applied according to the preset condition, the user's current state is not accurately reflected, and the desired state cannot be accurately maintained according to the user.

In addition, since audiovisual stimuli, etc. require concentration on the stimulus while the user is awake, it is difficult to be utilized during the user's sleeping time when the reaction to the external stimulus is maintained to the minimum level, or while the user is learning or working.

Further, since the conventional technology stimulates the user's brain, some users may feel uncomfortable and may cause undesired results due to side effects.

SUMMARY OF THE DISCLOSURE

One object of the present disclosure to solve some or all the aforementioned problems.

It is another object of the present disclosure to allow activities of the autonomic nervous system of a user to be induced.

It is still another object of the present disclosure to allow activities of the autonomic nervous system of the user to be induced by adjusting the characteristics of the stimulus while reflecting the current state of the user.

It is yet still another object of the present disclosure to allow activities of the autonomic nervous system of the user to be induced by user-specific stimulation.

In accordance with one aspect of the present disclosure, there is provided a method for inducing an activity of a user's autonomic nervous system, including steps of: (a) on condition that each of the user's reference heart rate information corresponding to each of active states of the user's autonomic nervous system is obtained, an inducing device, if a specific active state of the autonomic nervous system is selected by the user, acquiring first reference heart rate information of the user corresponding to the specific active state of the autonomic nervous system; and (b) the inducing device supporting a first vibration stimulus with a first period corresponding to the first reference heart rate information to be applied to the user, to thereby allow the user's real-time average cardiac interval to be synchronized with the first vibration stimulus.

As one example, at the step of (b), the inducing device sets the first period of the first vibration stimulus to a first average cardiac interval corresponding to the first reference heart rate information.

As one example, at the step of (b), (b1) on condition that the first vibration stimulus, which has a first average cardiac interval corresponding to the first reference heart rate information as the first period, is applied to the user, the inducing device obtains the user's real-time heart rate information and obtains the user's cardiac change rate by referring to the real-time heart rate information; and (b2) the inducing device maintains a state that the first vibration stimulus with the first period is applied to the user during a time when an active state value of a parasympathetic nerve at the user's cardiac change rate converges to a predetermined first reference value, wherein the predetermined first reference value is a maximum active state value of the parasympathetic nerve, which is obtained by the cardiac change rate in the active state of the user's specific autonomic nervous system.

As one example, at the step of (b2), the inducing device maintains a state of allowing the first vibration stimulus with the first period to be applied to the user during a time when the active state value of the parasympathetic nerve at the user's cardiac change rate converges to the predetermined first reference value and, at the same time, an active state value of a sympathetic nerve at the user's cardiac change rate converges to a predetermined second reference value, wherein the predetermined second reference value is a minimum active state value of the sympathetic nerve, which is obtained by the cardiac change rate in the active state of the user's specific autonomic nervous system.

As one example, the step (b) further includes a step of: (b3) on condition that the active state value of the parasympathetic nerve is less than the predetermined first reference value or does not converge to the predetermined first reference value, the inducing device gradually changes a period of the first vibration stimulus from an n-th period, corresponding to the real-time heart rate information, to the first period, and supports the first vibration stimulus with an (n-k)-th period, which is each changed period, to be applied to the user, to thereby allow the real-time average cardiac interval to be gradually synchronized with the first vibration stimulus.

As one example, at the step of (b3), on condition that (i) the active state value of the parasympathetic nerve is less than the predetermined first reference value or does not converge to the predetermined first reference value, and, at the same time, (ii) an active state value of a sympathetic nerve at the user's cardiac change rate exceeds a predetermined second reference value or does not converge to the predetermined second reference value, the inducing device gradually changes the period of the first vibration stimulus from the n-th period, corresponding to the real-time heart rate information, to the first period, and supports the first vibration stimulus with the (n-k)-th period, which is each changed period, to be applied to the user, to thereby allow the real-time average cardiac interval to be gradually synchronized with the first vibration stimulus, wherein the second reference value is a minimum active state value of the sympathetic nerve, which is obtained by the cardiac change rate in the active state of the user's specific autonomic nervous system.

As one example, at the step of (b), (b11) on condition that the first vibration stimulus, which has a first average cardiac interval corresponding to the first reference heart rate information as the first period, is applied to the user, the inducing device obtains the user's real-time heart rate information and obtains the user's cardiac change rate by referring to the real-time heart rate information; and (b12) the inducing device maintains a state that the first vibration stimulus with the first period is applied to the user during a time when an active state value of a sympathetic nerve at the user's cardiac change rate converges to a predetermined third reference value, wherein the predetermined third reference value is a maximum active state value of the sympathetic nerve, which is obtained by the cardiac change rate in the active state of the user's specific autonomic nervous system.

As one example, the step (b) further includes a step of: (b13) on condition that the active state value of the parasympathetic nerve is less than the predetermined third reference value or does not converge to the predetermined third reference value, the inducing device gradually changes a period of the first vibration stimulus from an n-th period, corresponding to the real-time heart rate information, to the first period, and supports the first vibration stimulus with an (n-k)-th period, which is each changed period, to be applied to the user, to thereby allow the real-time average cardiac interval to be gradually synchronized with the first vibration stimulus.

As one example, at the step of (b), (b4) the inducing device obtains the user's real-time heart rate information, supports the first vibration stimulus with an (n-k)-th period representing a period from an n-th period, which is a real-time average cardiac interval corresponding to the real-time heart rate information, to the first period, to be gradually applied to the user, obtains the user's cardiac change rate by referring to the user's gradually obtained real-time heart rate information, and maintains a state that the first vibration stimulus with the first period is applied to the user until an active state value of a parasympathetic nerve at the user's cardiac change rate reaches a predetermined first reference value, wherein the predetermined first reference value is a maximum active state value of the parasympathetic nerve, which is obtained by the cardiac change rate in the active state of the user's specific autonomic nervous system.

As one example, at the step of (b4), the inducing device maintains a state of allowing the first vibration stimulus to be applied to the user until the active state value of the parasympathetic nerve at the user's cardiac change rate reaches the predetermined first reference value, and an active state value of a sympathetic nerve at the user's cardiac change rate reaches a predetermined second reference value, wherein the predetermined second reference value is a minimum active state value of the sympathetic nerve, which is obtained by the cardiac change rate in the active state of the user's specific autonomic nervous system.

As one example, at the step of (b), (b14) the inducing device obtains the user's real-time heart rate information, supports the first vibration stimulus with an (n-k)-th period representing a period from an n-th period, which is a real-time average cardiac interval corresponding to the real-time heart rate information, to the first period, to be gradually applied to the user, obtains the user's cardiac change rate by referring to the user's gradually obtained real-time heart rate information, and maintains a state that the first vibration stimulus with the first period is applied to the user until an active state value of a sympathetic nerve at the user's cardiac change rate reaches a predetermined third reference value, wherein the predetermined third reference value is a maximum active state value of the sympathetic nerve, which is obtained by the cardiac change rate in the active state of the user's specific autonomic nervous system.

As one example, at the step of (b), (b5) the inducing device obtains the user's real-time heart rate information, obtains the user's cardiac change rate by referring to the real-time heart rate information, and supports a second vibration stimulus, which is generated by changing the first vibration stimulus, to be applied to the user if an active state value of a parasympathetic nerve at the user's cardiac change rate does not converge to a predetermined first reference value, wherein the predetermined first reference value is a maximum active state value of the parasympathetic nerve, which is obtained by the cardiac change rate in the active state of the user's specific autonomic nervous system.

As one example, at the step of (b), (b15) the inducing device obtains the user's real-time heart rate information, obtains the user's cardiac change rate by referring to the real-time heart rate information, and supports a third vibration stimulus, which is generated by changing the first vibration stimulus, to be applied to the user if an active state value of a sympathetic nerve at the user's cardiac change rate does not converge to a predetermined third reference value, wherein the predetermined third reference value is a maximum active state value of the sympathetic nerve, which is obtained by the cardiac change rate in the active state of the user's specific autonomic nervous system.

As one example, the first vibration stimulus is a non-recognized vibration stimulus which is not recognized by the user.

In accordance with another aspect of the present disclosure, there is provided an inducing device for inducing an activity of a user's autonomic nervous system, including: at least one storage unit that stores each of the user's reference heart rate information corresponding to each of active states of the user's autonomic nervous system; and at least one processor for performing processes of (I), if a specific active state of the autonomic nervous system is selected by the user, acquiring first reference heart rate information of the user corresponding to the specific active state of the autonomic nervous system, and (II) supporting a first vibration stimulus with a first period corresponding to the first reference heart rate information to be applied to the user, to thereby allow the user's real-time average cardiac interval to be synchronized with the first vibration stimulus.

As one example, at the process of (II), the processor sets the first period of the first vibration stimulus to a first average cardiac interval corresponding to the first reference heart rate information.

As one example, at the process of (II), the processor performs processes of: (II-1) on condition that the first vibration stimulus, which has a first average cardiac interval corresponding to the first reference heart rate information as the first period, is applied to the user, obtaining the user's real-time heart rate information and obtaining the user's cardiac change rate by referring to the real-time heart rate information; and (II-2) maintaining a state that the first vibration stimulus with the first period is applied to the user during a time when an active state value of a parasympathetic nerve at the user's cardiac change rate converges to a predetermined first reference value, wherein the predetermined first reference value is a maximum active state value of the parasympathetic nerve, which is obtained by the cardiac change rate in the active state of the user's specific autonomic nervous system.

As one example, at the step of (II-2), the processor maintains a state of allowing the first vibration stimulus with the first period to be applied to the user during a time when the active state value of the parasympathetic nerve at the user's cardiac change rate converges to the predetermined first reference value and, at the same time, an active state value of a sympathetic nerve at the user's cardiac change rate converges to a predetermined second reference value, wherein the predetermined second reference value is a minimum active state value of the sympathetic nerve, which is obtained by the cardiac change rate in the active state of the user's specific autonomic nervous system.

As one example, on condition that the active state value of the parasympathetic nerve is less than the predetermined first reference value or does not converge to the predetermined first reference value, the processor further performs a process of (II-3) gradually changing a period of the first vibration stimulus from an n-th period, corresponding to the real-time heart rate information, to the first period, and supporting the first vibration stimulus with an (n-k)-th period, which is each changed period, to be applied to the user, to thereby allow the real-time average cardiac interval to be gradually synchronized with the first vibration stimulus.

As one example, at the process of (II-3), on condition that (i) the active state value of the parasympathetic nerve is less than the predetermined first reference value or does not converge to the predetermined first reference value, and, at the same time, (ii) an active state value of a sympathetic nerve at the user's cardiac change rate exceeds a predetermined second reference value or does not converge to the predetermined second reference value, the processor gradually changes the period of the first vibration stimulus from the n-th period, corresponding to the real-time heart rate information, to the first period, and supports the first vibration stimulus with the (n-k)-th period, which is each changed period, to be applied to the user, to thereby allow the real-time average cardiac interval to be gradually synchronized with the first vibration stimulus, wherein the second reference value is a minimum active state value of the sympathetic nerve, which is obtained by the cardiac change rate in the active state of the user's specific autonomic nervous system.

As one example, at the process of (II), the processor performs processes of: (II-11) on condition that the first vibration stimulus, which has a first average cardiac interval corresponding to the first reference heart rate information as the first period, is applied to the user, obtaining the user's real-time heart rate information and obtaining the user's cardiac change rate by referring to the real-time heart rate information; and (II-12) maintaining a state that the first vibration stimulus with the first period is applied to the user during a time when an active state value of a sympathetic nerve at the user's cardiac change rate converges to a predetermined third reference value, wherein the predetermined third reference value is a maximum active state value of the sympathetic nerve, which is obtained by the cardiac change rate in the active state of the user's specific autonomic nervous system.

As one example, on condition that the active state value of the parasympathetic nerve is less than the predetermined third reference value or does not converge to the predetermined third reference value, the processor further performs a process of (II-13) gradually changing a period of the first vibration stimulus from an n-th period, corresponding to the real-time heart rate information, to the first period, and supporting the first vibration stimulus with an (n-k)-th period, which is each changed period, to be applied to the user, to thereby allow the real-time average cardiac interval to be gradually synchronized with the first vibration stimulus.

As one example, at the process of (II), the processor performs a process of: (II-4) obtaining the user's real-time heart rate information, supporting the first vibration stimulus with an (n-k)-th period representing a period from an n-th period, which is a real-time average cardiac interval corresponding to the real-time heart rate information, to the first period, to be gradually applied to the user, obtaining the user's cardiac change rate by referring to the user's gradually obtained real-time heart rate information, and maintaining a state that the first vibration stimulus with the first period is applied to the user until an active state value of a parasympathetic nerve at the user's cardiac change rate reaches a predetermined first reference value, wherein the predetermined first reference value is a maximum active state value of the parasympathetic nerve, which is obtained by the cardiac change rate in the active state of the user's specific autonomic nervous system.

As one example, at the process of (II-4), the processor maintains a state of allowing the first vibration stimulus to be applied to the user until the active state value of the parasympathetic nerve at the user's cardiac change rate reaches the predetermined first reference value, and an active state value of a sympathetic nerve at the user's cardiac change rate reaches a predetermined second reference value, wherein the predetermined second reference value is a minimum active state value of the sympathetic nerve, which is obtained by the cardiac change rate in the active state of the user's specific autonomic nervous system.

As one example, at the process of (II), the processor performs a process of: (II-14) obtaining the user's real-time heart rate information, supporting the first vibration stimulus with an (n-k)-th period representing a period from an n-th period, which is a real-time average cardiac interval corresponding to the real-time heart rate information, to the first period, to be gradually applied to the user, obtaining the user's cardiac change rate by referring to the user's gradually obtained real-time heart rate information, and maintaining a state that the first vibration stimulus with the first period is applied to the user until an active state value of a sympathetic nerve at the user's cardiac change rate reaches a predetermined third reference value, wherein the predetermined third reference value is a maximum active state value of the sympathetic nerve, which is obtained by the cardiac change rate in the active state of the user's specific autonomic nervous system.

As one example, at the process of (II), the processor performs a process of: (II-5) obtaining the user's real-time heart rate information, obtaining the user's cardiac change rate by referring to the real-time heart rate information, and supporting a second vibration stimulus, which is generated by changing the first vibration stimulus, to be applied to the user if an active state value of a parasympathetic nerve at the user's cardiac change rate does not converge to a predetermined first reference value, wherein the predetermined first reference value is a maximum active state value of the parasympathetic nerve, which is obtained by the cardiac change rate in the active state of the user's specific autonomic nervous system.

As one example, at the process of (II), the processor performs a process of: (II-15) obtaining the user's real-time heart rate information, obtaining the user's cardiac change rate by referring to the real-time heart rate information, and supporting a third vibration stimulus, which is generated by changing the first vibration stimulus, to be applied to the user if an active state value of a sympathetic nerve at the user's cardiac change rate does not converge to a predetermined third reference value, wherein the predetermined third reference value is a maximum active state value of the sympathetic nerve, which is obtained by the cardiac change rate in the active state of the user's specific autonomic nervous system.

As one example, the first vibration stimulus is a non-recognized vibration stimulus which is not recognized by the user.

BRIEF DESCRIPTION OF THE DRAWINGS

The above and other objects and features of the present disclosure will become apparent from the following description of preferred embodiments given in conjunction with the accompanying drawings, in which:

FIG. 5 schematically illustrates a cardiac change rate obtained in accordance with one example embodiment of the present disclosure.

DETAILED DESCRIPTION OF THE PREFERRED EMBODIMENTS

Figure 1:
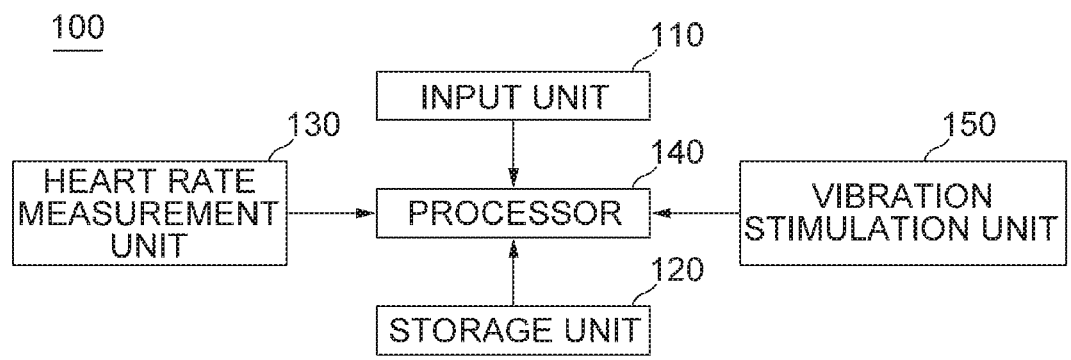
FIG. 1 schematically illustrates an apparatus for inducing an activity of a user's autonomic nervous system in accordance with one example embodiment of the present disclosure.

Detailed explanation on the present disclosure to be made below refer to attached drawings and diagrams illustrated as specific embodiment examples under which the present disclosure may be implemented to make clear of purposes, technical solutions, and advantages of the present disclosure. These embodiments are described in sufficient detail to enable those skilled in the art to practice the disclosure.

Besides, in the detailed description and claims of the present disclosure, a term "include" and its variations are not intended to exclude other technical features, additions, components or steps. Other objects, benefits, and features of the present disclosure will be revealed to one skilled in the art, partially from the specification and partially from the implementation of the present disclosure. The following examples and drawings will be provided as examples but they are not intended to limit the present disclosure.

Moreover, the present disclosure covers all possible combinations of example embodiments indicated in this specification. It is to be understood that the various embodiments of the present disclosure, although different, are not necessarily mutually exclusive. For example, a particular feature, structure, or characteristic described herein in connection with one embodiment may be implemented within other embodiments without departing from the spirit and scope of the present disclosure. In addition, it is to be understood that the position or arrangement of individual elements within each disclosed embodiment may be modified without departing from the spirit and scope of the present disclosure. The following detailed description is, therefore, not to be taken in a limiting sense, and the scope of the present disclosure is defined only by the appended claims, appropriately interpreted, along with the full range of equivalents to which the claims are entitled. In the drawings, like numerals refer to the same or similar functionality throughout the several views.

To allow those skilled in the art to the present disclosure to be carried out easily, the example embodiments of the present disclosure by referring to attached diagrams will be explained in detail as shown below.

FIG. 1 schematically illustrates an apparatus for inducing an activity of an autonomic nervous system in accordance with one example embodiment of the present disclosure. Referring to FIG. 1, an inducing device 100, i.e., a device for inducing an activity of autonomic nervous system, includes an input unit 110, a storage unit 120, a heart rate measurement unit 130, a processor 140, and a vibration stimulation unit 150.

The input unit 110 generates a signal according to an input operation of a user and may include a key pad, a mouse, a dome switch, a touch pad (static voltage/static current), a jog wheel, a jog switch, a microphone, and the like. However, the present disclosure is not limited to these examples and may include any device capable of generating an input signal according to a user's operation.

The storage unit 120 stores various data for operation of the inducing device 100 and may store the user's reference heart rate information corresponding to each of active states of the autonomic nervous system. Herein, the storage unit 120 may include at least one of a flash memory type, a hard disk type, a multimedia card micro type, a card type memory (for example, SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, and an optical disk. However, the present disclosure is not limited to these examples and may include all media capable of storing data. Alternatively, the storage unit 120 may be included inside the inducing device 100, or may be prepared separately from the inducing device 100 to transmit data or record received data through communication with the inducing device 100.

Next, the heart rate measurement unit 130 measures the heart rate of the user and may measure a ballistocardiogram, which is a minute tremble of a human body due to the heart beat of the user. Herein, the heart rate measurement unit 130 may be implemented in a non-restricting/non-contact manner with respect to the user's body. In addition, the heart rate measurement unit 130 may include a piezoelectric sensor for converting a pressure into an electric signal.

Next, in the state where the reference heart rate information of the user corresponding to each of the active states of the autonomic nervous system is stored in the storage unit 120, if the user selects a specific active state of the autonomic nervous system through the input unit 110, the processor 140 may check first reference heart rate information of the user corresponding to the specific active state of the autonomic nervous system and may support a first vibration stimulus having a first period corresponding to the checked first reference heart rate information to be applied to the user through the vibration stimulation unit 150, to thereby allow the user's real-time average cardiac interval to be synchronized with the first vibration stimulus.

Next, the vibration stimulation unit 150 may operate in response to a control signal from the processor 140 to thereby apply a vibration stimulus to the user. Herein, the vibration stimulus may be a non-recognized vibration stimulus which is a weak stimulus that the user cannot recognize.

Figure 2:
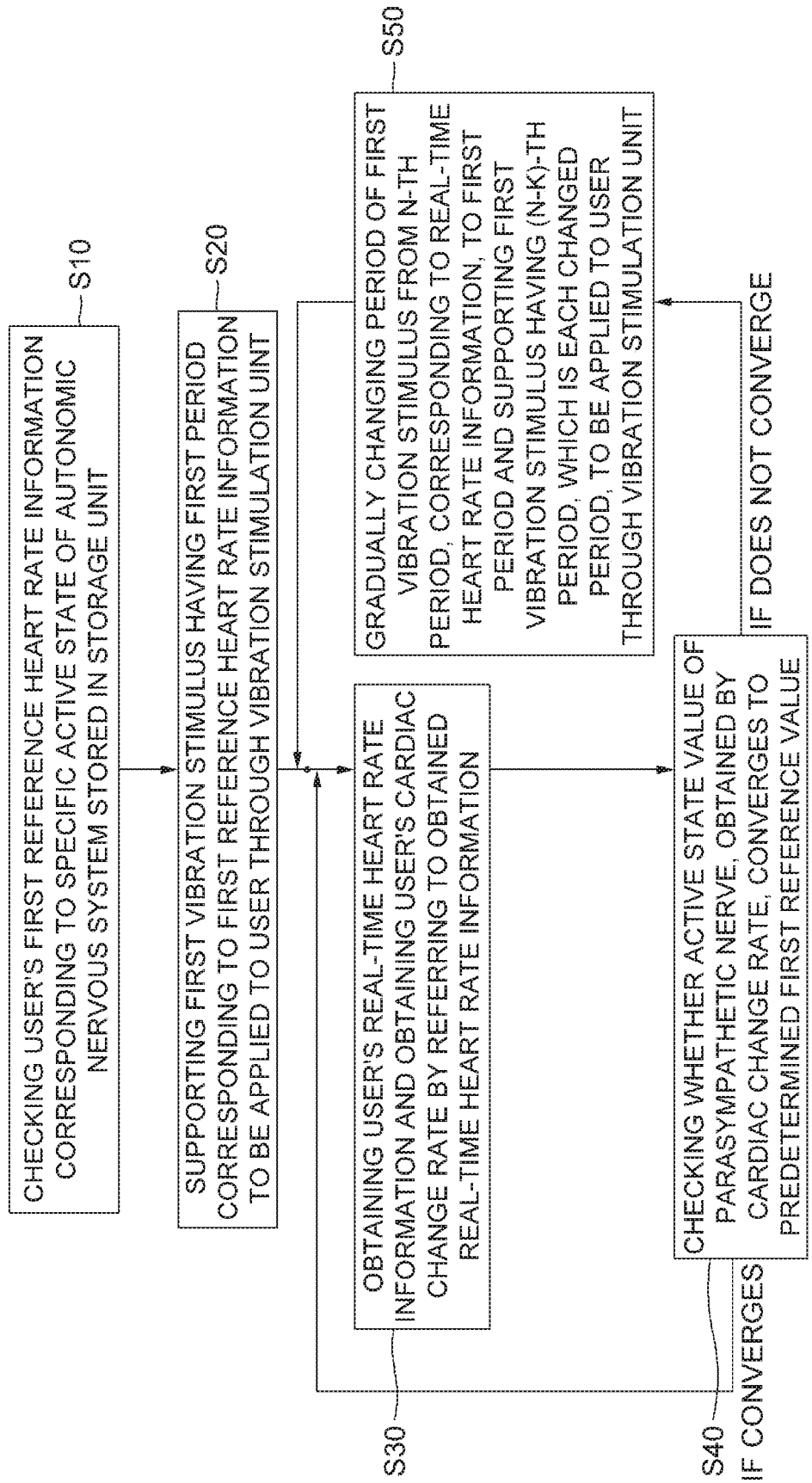
FIG. 2 schematically illustrates a method for inducing the activity of the user's autonomic nervous system in accordance with one example embodiment of the present disclosure.

A method for inducing the activity of the user's autonomic nervous system by using the inducing device 100 in accordance with one example embodiment of the present disclosure will be described below with reference to FIG. 2.

First, the user's reference heart rate information according to each of active states of the autonomic nervous system may be stored in the storage unit 120. At this time, the reference heart rate information may be information on the heart rate of the user detected in each of the active states of the autonomic nervous system. For example, the reference heart rate information may be the user's average cardiac interval which is detected in the state that the user's autonomic nervous system is stable. In addition, the active state of the autonomic nervous system may include a sleep mode, a concentration improvement mode, a stress relaxation mode, a cardiovascular stable mode, an emotion mode, and the like. The sleep mode may include a deep sleep mode, an REM sleep mode, a sleep maintenance mode, a wake-up mode, and the emotion mode may include a stable mode, a comfortable mode, and a wake-up mode.

In a state that the user's reference heart rate information corresponding to each of the active states of the autonomic nervous system is acquired, if the user selects a specific active state of the autonomic nervous system through the input unit 110 in order to induce a specific activity of the user's autonomic nervous system, the processor 140 of the inducing device 100 checks the user's first reference heart rate information corresponding to the specific active state of the autonomic nervous system stored in the storage unit 120 at the step of S10.

Then, the processor 140 supports the first vibration stimulus having the first period corresponding to the first reference heart rate information to be applied to the user through the vibration stimulation unit 150 at the step of S20, to thereby allow the user's real-time average cardiac interval to be synchronized with the first vibration stimulus. Herein, the first period of the first vibration stimulus may be the first average cardiac interval corresponding to the first reference heart rate information. That is, the processor 140 may check the average cardiac interval from the first reference heart rate information corresponding to the specific activity of the autonomic nervous system, may generate a first vibration stimulus signal having the checked average cardiac interval as the first period, and may control the vibration stimulation unit 150 by using the generated first vibration stimulus signal having the first period, to thereby allow the vibration stimulation unit 150 to allow the first vibration stimulus having the first period to be applied to the user. In addition, the first vibration stimulus may be a non-recognized vibration stimulus that the user cannot recognize, which does not disturb the user's current activity.

Figure 3:
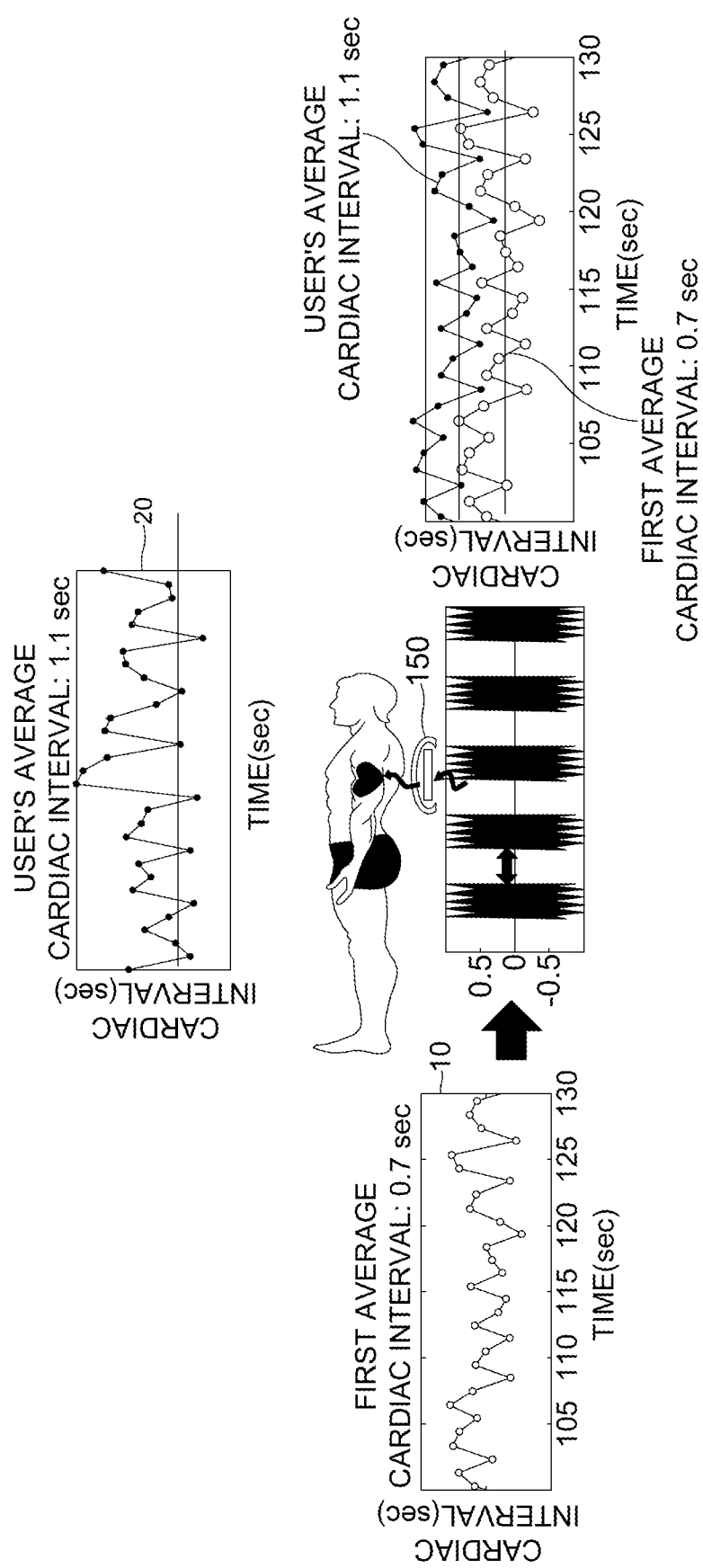
FIG. 3 schematically illustrates a state of acquiring heart rate information of the user in accordance with one example embodiment of the present disclosure.

As such, as illustrated in FIG. 3, the user's average cardiac interval 20 is synchronized with the first vibration stimulus by the vibration stimulation unit 150, and consequently, the user's real-time average cardiac interval 20 converges to a first average cardiac interval 10 corresponding to the reference heart rate information in the specific active state of the autonomic nervous system stored in the storage unit 120. Then, as the user's real-time average cardiac interval 20 converges to the first average cardiac interval 10, the active state of the user's autonomic nervous system may be induced to the specific active state of the autonomic nervous system selected by the user.

That is, an inner control function, which is a main function of the autonomic nervous system, may be maximized by inducing the active state of autonomic nervous system in a direction desired by the user. This can be applied to assistive technologies for treating cardiovascular diseases, induction of sleep, and the like in the medical field, and can be applied to stress relaxation technologies in the health care field. This can also be used for learning, improving work concentration, and controlling emotions, and the like.

For example, deep sleep is related to physical recovery, growth hormone acceleration, and narrative memory enhancement, and REM sleep is related to procedural memory, creativity, and depression. Thus, sleep function may be maximized by inducing specific active states of the autonomic nervous system such as deep sleep or REM sleep at the same sleeping time. In addition, daily stress relief, tension control, and concentration improvement can be expected, which may improve job performance and health. Furthermore, this can assist cardiovascular activities of unhealthy persons and can be used as health related indicators.

In addition, on condition that the first vibration stimulus having the first average cardiac interval as the first period is supported to be applied to the user through the vibration stimulation unit 150, the processor 140 of the inducing device 100 obtains the user's real-time heart rate information and obtains the user's cardiac change rate by referring to the obtained real-time heart rate information at the step of S30.

Figure 4A:
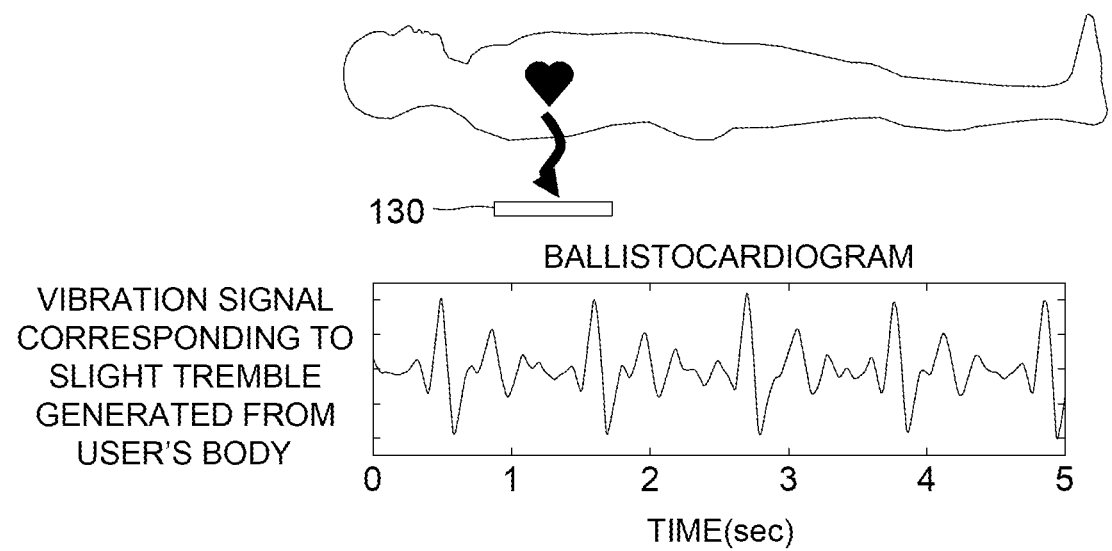
FIG. 4A schematically illustrates a state in which a user's heartbeat is synchronized in accordance with one example embodiment of the present disclosure.
Figure 4B:
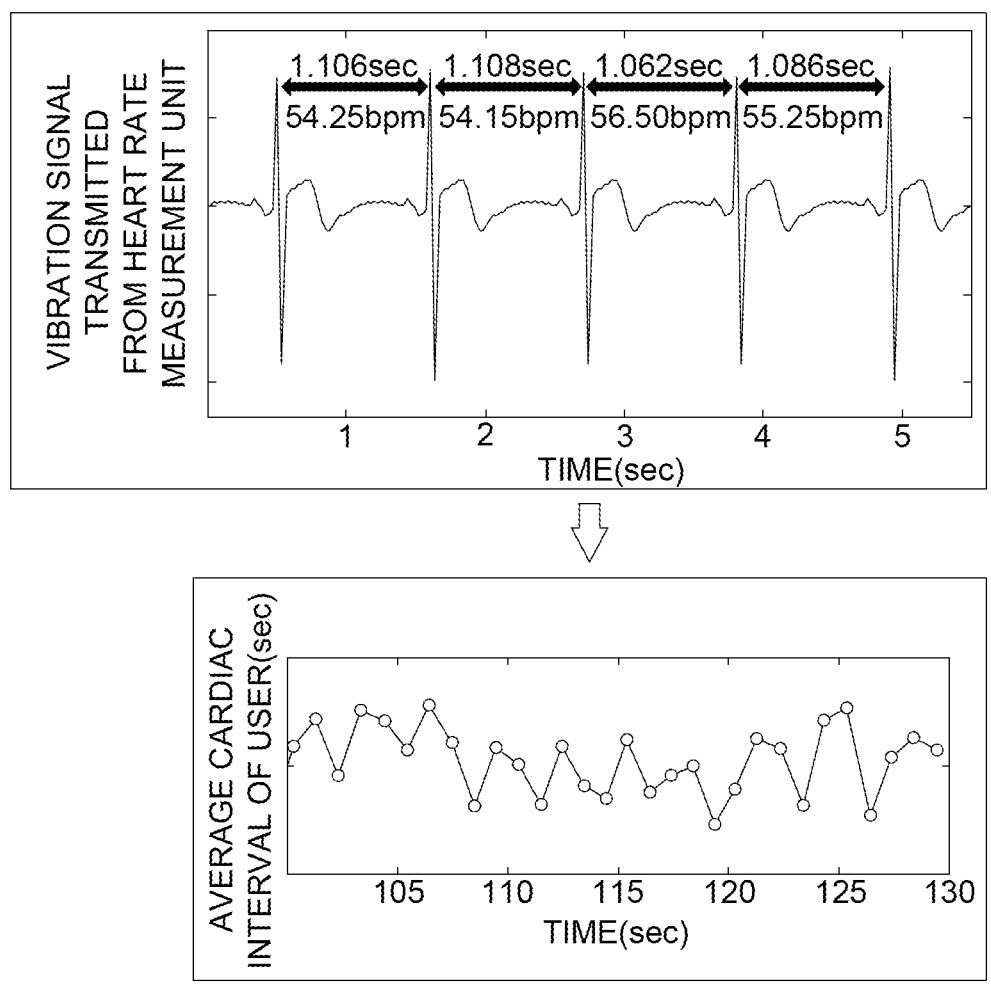
FIG. 4B schematically illustrates a vibration signal transmitted from the heart rate measurement unit in accordance with one example embodiment of the present disclosure.

For example, as shown in FIG. 4A, if the current activity of the user is not disturbed by the non-restricting/non-contact scheme and the heart rate measurement unit 130 obtains a vibration signal corresponding to a slight tremble generated from the user's body and transmits the vibration signal, the processor 140 analyzes the vibration signal transmitted from the heart rate measurement unit 130 as shown in FIG. 4B to thereby obtain the average cardiac interval of the user. Herein, since the vibration signal obtained from the heart rate measurement unit 130 may include a vibration signal applied to the user by the vibration stimulation unit 150, the vibration signal applied to the user by the vibration stimulation unit 150 is removed from the vibration signal obtained from the heart rate measurement unit 130 to thereby obtain the user's ballistocardiogram. Further, the ballistocardiogram is treated with the heart rate band, and the heart rate is calculated by using the periodic characteristic of the heart rate.

Thereafter, the processor 140 obtains the user's cardiac change rate, which is generated by quantifying the minute degree of change of the user's cardiac interval by referring to the heart rate as shown in FIG. 5. Herein, the time domain in the cardiac change rate may be quantified by using the (number of) average cardiac change rate and the standard deviation of the cardiac interval, and the frequency domain in the cardiac change rate may be quantified by calculating the power per frequency band of the cardiac interval. VLF is a power in a band from 0 Hz to 0.04 Hz, LF is a power in a band from 0.04 Hz to 0.15 Hz, and HF is a power in a band from 015 Hz to 0.4 Hz. Further, LFHF is LF/HF, nHF is HF/(LF+HF), and nLF is LF/(LF+HF).

Herein, HF and nHF are mainly used to observe the activity of the parasympathetic nerve, and VLF, LF, nLF, and LFHF are mainly used to observe the activity of the sympathetic nerve.

Next, the processor 140 supports the first vibration stimulus having the first period to be continually applied to the user through the vibration stimulation unit 150 during a time when the active state value of the parasympathetic nerve in the cardiac change rate, such as HF or nHF, converges to a predetermined first reference value. Herein, the predetermined first reference value may be the maximum active state value of the parasympathetic nerve, which is obtained by the cardiac change rate in a specific active state of the user's autonomic nervous system.

For example, the processor 140 checks whether the active state value of the parasympathetic nerve, obtained by the cardiac change rate, converges to the predetermined first reference value at the step of S40.

As a result of the checking, if the obtained active state value of the parasympathetic nerve converges to the first reference value, the processor 140 allows the first vibration stimulus having the first period to be continually applied to the user through the vibration stimulation unit 150.

However, if the obtained active state value of the parasympathetic nerve does not converge to the first reference value, namely, the obtained active state value of the parasympathetic nerve is not changed at a value less than the first reference value or does not converge to the predetermined first reference value, the processor 140 gradually changes the period of the first vibration stimulus from an n-th period, corresponding to the real-time heart rate information, to the first period and supports the first vibration stimulus having an (n-k)-th period, which is each changed period, to be applied to the user through the vibration stimulation unit 150 at the step of S50, to thereby allow the real-time average cardiac interval to be gradually synchronized with the first vibration stimulus.

Namely, if the active state value of the parasympathetic nerve does not converge to the first reference value, the processor 140 minimizes a target value for synchronization by adjusting the period of the first vibration stimulus to become similar to the user's real-time average cardiac interval, to thereby allow the user's real-time average cardiac interval to be easily synchronized with the first vibration stimulus. Further, the (n-k)-th period, which is the period of the first vibration stimulus for synchronization, may be allowed to be gradually changed from the n-th period to the first period and may be allowed to be finally synchronized with the first period by repeating the operation of the user's real-time average cardiac interval to be synchronized gradually.

In the above, the active state value of the parasympathetic nerve of the cardiac change rate was compared with the predetermined first reference value in order to check whether the active state of the user's autonomic nervous system was induced to the specific active state of the autonomic nervous system, intended by the user. However, the active state value of the sympathetic nerve (VLF, LF, nLF, or LFHF) of the cardiac change rate may be additionally checked.

Namely, the processor 140 of the inducing device 100 may allow the first vibration stimulus having the first period or the (n-k)-th period to be continually applied to the user through the vibration stimulation unit 150 during a time when the active state value of the parasympathetic nerve in the cardiac change rate converges to the first reference value and, at the same time, the active state value of the sympathetic nerve in the cardiac change rate converges to a predetermined second reference value. Herein, the predetermined second reference value may be the minimum active state value of the sympathetic nerve, which is obtained by the cardiac change rate in a specific active state of the user's autonomic nervous system.

Further, if the active state value of the user's parasympathetic nerve is less than the predetermined first reference value or does not converge to the predetermined first reference value and, at the same time, the active state value of the sympathetic nerve in the cardiac change rate exceeds the predetermined second reference value or does not converge to the predetermined second reference value, the processor 140 of the inducing device 100 gradually changes the period of the first vibration stimulus from the n-th period, corresponding to the real-time heart rate information, to the first period, and supports the first vibration stimulus having the (n-k)-th period, each changed period, to be applied to the user through the vibration stimulation unit 150, to thereby allow the real-time average cardiac interval to be gradually synchronized with the first vibration stimulus.

As mentioned above, the processor 140 of the inducing device 100 allows the first vibration stimulus having the first period to be applied to the user, then changes the period of the first vibration stimulus according to the user's current state by referring to the user's cardiac change rate.

However, as another example, the processor 140 may gradually change the period of the first vibration stimulus from the n-th period to the first period and may support the first vibration stimulus having the (n-k)-th period to be applied to the user through the vibration stimulation unit 150.

Namely, the processor 140 of the inducing device 100 may obtain the user's real-time heart rate information and may support the first vibration stimulus having the (n-k)-th period representing a period from the n-th period, which is a real-time average cardiac interval corresponding to the real-time heart rate information, to the first period, to be gradually applied to the user through the vibration stimulation unit 150. Further, the user's cardiac change rate may be obtained by referring to the user's real-time heart rate information obtained in each step, and the first vibration stimulus may be continually applied to the user until the active state value of the user's parasympathetic nerve in the cardiac change rate reaches the predetermined first reference value. Further, the processor 140 of the inducing device 100 may allow the first vibration stimulus to be continually applied to the user through the vibration stimulation unit 150 until the active state value of the user's parasympathetic nerve in the cardiac change rate reaches the predetermined first reference value and the active state value of the sympathetic nerve reaches the predetermined second reference value.

In addition, the processor 140 of the inducing device 100 may obtain the user's real-time heart rate information and obtain the cardiac change rate by referring to the user's real-time heart rate information, and if the active state value of the user's parasympathetic nerve in the cardiac change rate does not converge to the predetermined first reference value, the processor 140 may support the second vibration stimulus, which is generated by changing the first vibration stimulus, to be applied to the user.

Namely, if the intensity of the first vibration stimulus becomes recognizable by the user, the user's current activity may be disturbed by the first vibration stimulus, thereby making it impossible to be induced to the active state of the autonomic nervous system, desired by the user. Herein, the active state value of the parasympathetic nerve in the cardiac change rate may become further away from the first reference value. Therefore, the processor 140 may change the first vibration stimulus to the second vibration stimulus, which is a non-recognized vibration stimulus, by lowering its intensity, and may allow the second vibration stimulus to be applied to the user through the vibration stimulation unit 150. Further, the processor 140 may store the second vibration stimulus having the changed intensity in the storage unit 120 as stimulus information corresponding to a specific active state of the user's autonomic nervous system, or may update the stored stimulus information.

Further, if it is determined that the active state of the user's autonomic nervous system is induced to a user-desired specific active state of the autonomic nervous system in the process of inducing the active state of the user's autonomic nervous system in various above-described methods, namely, in the state where the active state value of the user's parasympathetic nerve in the cardiac change rate becomes the first reference value or the active state value of the sympathetic nerve becomes the second reference value, the processor 140 of the inducing device 100 may obtain the user's real-time heart rate information, may update the obtained real-time heart rate information to become reference heart rate information corresponding to the specific active state of the user's autonomic nervous system, and may record the updated information in the storage unit 120.

The method of inducing the activity of the autonomic nervous system in accordance with one example embodiment of the present disclosure can be applied to induction of sleep, improvement of concentration, emotion/stress control, cardiovascular regulation, utilization as a health index.

For example, in case the method of inducing the activity of the autonomic nervous system is applied to the induction of sleep, if the user sets a deep sleep mode (active state of the parasympathetic nerve) before sleeping, the processor 140 calls in characteristics of the heart rate of the user's deep sleep, stored in the storage unit 120, then generates the stimulus signal according to the biorhythm characteristics and delivers the generated stimulus signal. Further, the processor 140 analyzes the active state of the user's autonomic nervous system by using the heart rate which is measured in a non-restricting manner, and if the activation level of the parasympathetic nerve has not increased, the processor 140 changes the stimulus signal by reflecting the characteristics of the current heart rate thereon to thereby regenerate and deliver the changed stimulus. Further, the processor 140 determines the user's sleep phase by using the current heart rate, and if the deep sleep time is less than a reference time, the processor 140 continually provides stimulation for activation of the parasympathetic nerve. Further, if the active state of the parasympathetic nerve is in the maximum level, the processor 140 updates the characteristics of the heart rate in the storage unit 120. Further, if the user desires REM sleep as well as deep sleep, its corresponding stimulus signal is generated and delivered.

Next, when the method of inducing the activity of the autonomic nervous system in accordance with one example embodiment of the present disclosure is applied to the concentration enhancement, if the user wants to concentrate and selects the concentration mode, the processor 140 grasps the current heart rate characteristics and determines the current state of the autonomic nervous system, and determines the size and the intensity of the stimulus signal within a range similar to that of the current heart rate. Further, the processor 140 observes the cardiac change rate shown during concentration and, if such characteristics are not shown, the processor 140 changes the characteristics of the stimulus.

Next, when the method of inducing the activity of the autonomic nervous system in accordance with one example embodiment of the present disclosure is applied to emotion/stress control, if the user selects a relaxation mode such as relaxation, peace, balance, or wake-up, the processor 140 determines the current state of the autonomic nervous system by grasping the current characteristics of the heart rate and determines the size and the intensity of the stimulus signal within a range similar to that of the current cardiac interval. Further, the processor 140 observes the active state of the parasympathetic nerve by analyzing the characteristics of the current heart rate according to stimulus, and if there is few changes in the activity of the parasympathetic nerve, the processor 140 adjusts the size and the intensity of the stimulus. Further, the processor 140 observes the activity of the parasympathetic nerve, and if the active state is in the maximum level, the processor 140 updates the characteristics of the heart rate in the storage unit 120.

Next, when the method of inducing the activity of the autonomic nervous system in accordance with one example embodiment of the present disclosure is applied to the cardiovascular regulation, the processor 140 determines the tachycardia and bradycardia by grasping the current heartbeat characteristics, and generates and delivers a stimulus for relieving the current state. For example, if the user has tachycardia, the stimulus signal is delivered within a range similar to that of the current heart rate, and the heart rate is lowered by gradually lowering the stimulus frequency.

Next, when the method of inducing the activity of the autonomic nervous system in accordance with one example embodiment of the present disclosure is applied to the utilization of the health index, the processor 140 determines the intensity and the size of the stimulus by using the characteristics of the heart rate corresponding to the activation of the sympathetic nerve/parasympathetic nerve, and the activation of the sympathetic nerve/parasympathetic nerve then gives the stimulus, and quantifies mutual characteristics between the external stimulus and the heartbeat. Then, the quantified value is compared with the reference value and is utilized as health indexes of the heart-lung, cardiovascular system and autonomic nervous system.

Although the above description has centered on the active state of the parasympathetic nerve, the same method may be applied to the active state of the sympathetic nerve.

Namely, the processor 140 supports the first vibration stimulus having the first period to be continually applied to the user through the vibration stimulation unit 150 during a time when the active state value of the sympathetic nerve in the cardiac change rate, such as VLF, LF, nHF, or LFHF converges to a predetermined third reference value. Herein, the predetermined third reference value may be the maximum active state value of the sympathetic nerve, which is obtained by the cardiac change rate in a specific active state of the user's autonomic nervous system.

For example, the processor 140 determines whether the active state value of the sympathetic nerve, obtained by the cardiac change rate, converges to the predetermined third reference value, and if the obtained active state value of the sympathetic nerve converges to the third reference value as a result of the determination, the processor 140 allows the first vibration stimulus having the first period to be continuously applied to the user through the vibration stimulation unit 150.

However, if the obtained active state value of the sympathetic nerve does not converge to the third reference value, namely, the obtained active state value of the sympathetic nerve is not changed at a value less than the third reference value or does not converge to the predetermined third reference value, the processor 140 gradually changes the period of the first vibration stimulus from an n-th period, corresponding to the real-time heart rate information, to the first period and supports the first vibration stimulus having an (n-k)-th period, which is each changed period, to be applied to the user through the vibration stimulation unit 150, to thereby allow the real-time average cardiac interval to be gradually synchronized with the first vibration stimulus.

Namely, if the active state value of the sympathetic nerve does not converge to the third reference value, the processor 140 minimizes a target value for synchronization by adjusting the period of the first vibration stimulus to become similar to the user's real-time average cardiac interval, to thereby allow the user's real-time average cardiac interval to be easily synchronized with the first vibration stimulus. Further, the (n-k)-th period, which is the period of the first vibration stimulus for synchronization, may be allowed to be gradually changed and may be allowed to be finally synchronized with the first period by repeating the operation of the user's real-time average cardiac interval to be synchronized gradually.

In the above, the active state value of the sympathetic nerve of the cardiac change rate was compared with the predetermined third reference value in order to check whether the active state of the user's autonomic nervous system was induced to the specific active state of the autonomic nervous system, intended by the user. However, the active state value of the parasympathetic nerve of the cardiac change rate may be additionally checked.

Namely, the processor 140 of the inducing device 100 may allow the first vibration stimulus having the first period or the (n-k)-th period to be continually applied to the user through the vibration stimulation unit 150 during a time when the active state value of the sympathetic nerve in the cardiac change rate converges to the third reference value and, at the same time, the active state value of the parasympathetic nerve in the cardiac change rate converges to a predetermined fourth reference value. Herein, the predetermined fourth reference value may be the minimum active state value of the parasympathetic nerve, which is obtained by the cardiac change rate in a specific active state of the user's autonomic nervous system.

Further, if the active state value of the user's sympathetic nerve is less than the predetermined third reference value or does not converge to the predetermined third reference value and, at the same time, the active state value of the parasympathetic nerve in the cardiac change rate exceeds the predetermined fourth reference value or does not converge to the predetermined fourth reference value, the processor 140 of the inducing device 100 gradually changes the period of the first vibration stimulus from the n-th period, corresponding to the real-time heart rate information, to the first period, and supports the first vibration stimulus having the (n-k)-th period, each changed period, to be applied to the user through the vibration stimulation unit 150, to thereby allow the real-time average cardiac interval to be gradually synchronized with the first vibration stimulus.

As mentioned above, the processor 140 of the inducing device 100 allows the first vibration stimulus having the first period to be applied to the user, then changes the period of the first vibration stimulus according to the user's current state by referring to the user's cardiac change rate. However, as another example, the processor 140 may gradually change the period of the first vibration stimulus from the n-th period to the first period and may support the first vibration stimulus having the (n-k)-th period to be applied to the user through the vibration stimulation unit 150.

Namely, the processor 140 of the inducing device 100 may obtain the user's real-time heart rate information and may support the first vibration stimulus having the (n-k)-th period representing a period from the n-th period, which is a real-time average cardiac interval corresponding to the real-time heart rate information, to the first period, to be gradually applied to the user through the vibration stimulation unit 150. Further, the user's cardiac change rate may be obtained by referring to the user's real-time heart rate information obtained in each step, and the first vibration stimulus may be continually applied to the user until the active state value of the user's sympathetic nerve in the cardiac change rate reaches the predetermined third reference value. Further, the processor 140 of the inducing device 100 may allow the first vibration stimulus to be continually applied to the user through the vibration stimulation unit 150 until the active state value of the user's sympathetic nerve in the cardiac change rate reaches the predetermined fourth reference value and the active state value of the parasympathetic nerve reaches the predetermined fourth reference value.

In addition, the processor 140 of the inducing device 100 may obtain the user's real-time heart rate information and obtain the cardiac change rate by referring to the user's real-time heart rate, and if the active state value of the user's sympathetic nerve in the cardiac change rate does not converge to the predetermined third reference value, the processor 140 may support the third vibration stimulus, which is generated by changing the first vibration stimulus, to be applied to the user.

For example, in order to induce wake-up of the user from the sleep state, the processor 140 may gradually adjust the activity of the user's autonomic nervous system before the user's wake-up time, that is, may activate the sympathetic nerve to thereby induce a more stable, comfortable wake-up.

That is, if the user sets the wake-up mode (activated state of the sympathetic nerve), the processor 140 invokes the characteristics of the heart rate corresponding to the user's wake-up, stored in the storage unit 120, before the wake-up time which is set by the user, then generates a stimulus signal according to the corresponding biorhythm characteristics and delivers the generated stimulus signal to the user. Further, the processor 140 analyzes the active state of the user's autonomic nervous system by using the heart rate which is measured in a non-restricting manner, and if the activation level of the sympathetic nerve has not increased, the processor 140 changes the stimulus signal by reflecting the characteristics of the current heart rate thereon to thereby regenerated and deliver the changed stimulus. This allows the processor 140 to induce the stable wake-up of the user.

The present disclosure has an effect of allowing the internal environment of the user's body to be maintained because the user can induce the activity of the autonomic nervous system in a user-desired state.

The present disclosure has another effect of accurately inducing the activity of the autonomic nervous system in the user-desired state by adjusting the characteristics of the stimulus while reflecting the user's current state.

The present disclosure has still another effect of preventing side effects according to the user's personal characteristics by inducing the activity of the user's autonomic nervous system through user-specific stimuli.

The embodiments of the present disclosure as explained above can be implemented in a form of executable program command through a variety of computer means recordable to computer readable media. The computer readable media may include solely or in combination, program commands, data files, and data structures. The program commands recorded to the media may be components specially designed for the present disclosure or may be usable to a skilled human in a field of computer software. Computer readable media include magnetic media such as hard disk, floppy disk, and magnetic tape, optical media such as CD-ROM and DVD, magneto-optical media such as floptical disk and hardware devices such as ROM, RAM, and flash memory specially designed to store and carry out program commands. Program commands include not only a machine language code made by a complier but also a high level code that can be used by an interpreter etc., which is executed by a computer. The aforementioned hardware device can work as more than a software module to perform the action of the present disclosure and they can do the same in the opposite case.

As seen above, the present disclosure has been explained by specific matters such as detailed components, limited embodiments, and drawings. While the disclosure has been shown and described with respect to the preferred embodiments, it, however, will be understood by those skilled in the art that various changes and modification may be made without departing from the spirit and scope of the disclosure as defined in the following claims.

Accordingly, the thought of the present disclosure must not be confined to the explained embodiments, and the following patent claims as well as everything including variations equal or equivalent to the patent claims, pertain to the category of the thought of the present disclosure.

What is claimed is:

1. A method for inducing an activity of a user's autonomic nervous system, comprising steps of:
   (a) on condition that each of the user's reference heart rate information corresponding to each of active states of the user's autonomic nervous system is obtained, an inducing device, if a specific active state of the user's autonomic nervous system is selected by the user, acquiring first reference heart rate information of the user corresponding to the specific active state of the user's autonomic nervous system;
   (b) the inducing device supporting a first vibration stimulus with a first period corresponding to the first reference heart rate information to be applied to the user by a vibration stimulation unit of the inducing device, to thereby allow the user's real-time average cardiac interval to be synchronized with the first vibration stimulus;
   (b1) on condition that the first vibration stimulus, which has a first average cardiac interval corresponding to the first reference heart rate information as the first period, is applied to the user, a heart rate measurement unit of the inducing device obtains the user's real-time heart rate information and obtains the user's cardiac change rate by referring to the real-time heart rate information;
   (b2) when an active state value of a parasympathetic nerve at the user's cardiac change rate converges to a predetermined first reference value, the inducing device maintains a state that the first vibration stimulus with the first period is applied to the user during a time;
   (b3) on condition that the active state value of the parasympathetic nerve is less than the predetermined first reference value or does not converge to the predetermined first reference value, the inducing device gradually changes a period of the first vibration stimulus from an n-th period, corresponding to the real-time heart rate information, to the first period, and supports the first vibration stimulus with an (n-k)-th period, which is each changed period, to be applied to the user, to thereby allow the real-time average cardiac interval to be gradually synchronized with the first vibration stimulus;
   (b4) when an active state value of a sympathetic nerve at the user's cardiac change rate converges to a predetermined second reference value, the inducing device maintains a state that the first vibration stimulus with the first period is applied to the user during a time; and
   (b5) on condition that the active state value of the sympathetic nerve is less than the predetermined second reference value or does not converge to the predetermined second reference value, the inducing device gradually changes the period of the first vibration stimulus from the n-th period, corresponding to the real-time heart rate information, to the first period, and supports the first vibration stimulus with the (n-k)-th period, which is each changed period, to be applied to the user, to thereby allow the real-time average cardiac interval to be gradually synchronized with the first vibration stimulus,
   wherein the predetermined first reference value is a maximum active state value of the parasympathetic nerve and the predetermined second reference value is a maximum active state value of the sympathetic nerve, both of which are obtained by the cardiac change rate in the specific active state of the user's autonomic nervous system.

2. The method of claim 1, wherein, at the step of (b), the inducing device sets the first period of the first vibration stimulus to the first average cardiac interval corresponding to the first reference heart rate information.

3. The method of claim 1, wherein, at the step of (b2), the inducing device maintains a state of allowing the first vibration stimulus with the first period to be applied to the user during a time when the active state value of the parasympathetic nerve at the user's cardiac change rate converges to the predetermined first reference value and, at the same time, the active state value of the sympathetic nerve at the user's cardiac change rate converges to a predetermined third reference value,
wherein the predetermined third reference value is a minimum active state value of the sympathetic nerve, which is obtained by the cardiac change rate in the specific active state of the user's autonomic nervous system.

4. The method of claim 1, wherein, at the step of (b3), on condition that (i) the active state value of the parasympathetic nerve is less than the predetermined first reference value or does not converge to the predetermined first reference value, and, at the same time, (ii) the active state value of the sympathetic nerve at the user's cardiac change rate exceeds a predetermined third reference value or does not converge to the predetermined third reference value, the inducing device gradually changes the period of the first vibration stimulus from the n-th period, corresponding to the real-time heart rate information, to the first period, and supports the first vibration stimulus with the (n-k)-th period, which is each changed period, to be applied to the user, to thereby allow the real-time average cardiac interval to be gradually synchronized with the first vibration stimulus,
wherein the third reference value is a minimum active state value of the sympathetic nerve, which is obtained by the cardiac change rate in the specific active state of the user's autonomic nervous system.

5. The method of claim 1, wherein, at the step of (b),
(b6) the inducing device obtains the user's real-time heart rate information, supports the first vibration stimulus with the (n-k)-th period representing the period from the n-th period, which is the user's real-time average cardiac interval corresponding to the real-time heart rate information, to the first period, to be gradually applied to the user, obtains the user's cardiac change rate by referring to the user's gradually obtained real-time heart rate information, and maintains a state that the first vibration stimulus with the first period is applied to the user until the active state value of the parasympathetic nerve at the user's cardiac change rate reaches the predetermined first reference value,
wherein the predetermined first reference value is the maximum active state value of the parasympathetic nerve, which is obtained by the cardiac change rate in the specific active state of the user's autonomic nervous system.

6. The method of claim 5, wherein, at the step of (b6), the inducing device maintains a state of allowing the first vibration stimulus to be applied to the user until the active state value of the parasympathetic nerve at the user's cardiac change rate reaches the predetermined first reference value, and the active state value of the sympathetic nerve at the user's cardiac change rate reaches a predetermined third reference value,
wherein the predetermined third reference value is a minimum active state value of the sympathetic nerve, which is obtained by the cardiac change rate in the specific active state of the user's autonomic nervous system.

7. The method of claim 1, wherein, at the step of (b),
(b7) the inducing device obtains the user's real-time heart rate information, supports the first vibration stimulus with the (n-k)-th period representing the period from the n-th period, which is the user's real-time average cardiac interval corresponding to the real-time heart rate information, to the first period, to be gradually applied to the user, obtains the user's cardiac change rate by referring to the user's gradually obtained real-time heart rate information, and maintains a state that the first vibration stimulus with the first period is applied to the user until the active state value of the sympathetic nerve at the user's cardiac change rate reaches the predetermined second reference value,
wherein the predetermined second reference value is the maximum active state value of the sympathetic nerve, which is obtained by the cardiac change rate in the specific active state of the user's autonomic nervous system.

8. The method of claim 1, wherein, at the step of (b),
(b8) the inducing device obtains the user's real-time heart rate information, obtains the user's cardiac change rate by referring to the real-time heart rate information, and supports a second vibration stimulus, which is generated by changing the first vibration stimulus, to be applied to the user if the active state value of the parasympathetic nerve at the user's cardiac change rate does not converge to the predetermined first reference value,
wherein the predetermined first reference value is the maximum active state value of the parasympathetic nerve, which is obtained by the cardiac change rate in the specific active state of the user's autonomic nervous system.

9. The method of claim 1, wherein, at the step of (b),
(b9) the inducing device obtains the user's real-time heart rate information, obtains the user's cardiac change rate by referring to the real-time heart rate information, and supports a third vibration stimulus, which is generated by changing the first vibration stimulus, to be applied to the user if the active state value of the sympathetic nerve at the user's cardiac change rate does not converge to the predetermined second reference value,
wherein the predetermined second reference value is the maximum active state value of the sympathetic nerve, which is obtained by the cardiac change rate in the specific active state of the user's autonomic nervous system.

10. The method of claim 1, wherein the first vibration stimulus is a non-recognized vibration stimulus which is not recognized by the user.

11. An inducing device for inducing an activity of a user's autonomic nervous system, comprising:
at least one storage unit that stores each of the user's reference heart rate information corresponding to each of active states of the user's autonomic nervous system;
at least one processor for performing processes of:
(I) if a specific active state of the user's autonomic nervous system is selected by the user, acquiring first reference heart rate information of the user corresponding to the specific active state of the user's autonomic nervous system;

(II) configuring a vibration stimulation unit to support a first vibration stimulus with a first period corresponding to the first reference heart rate information to be applied to the user, to thereby allow the user's real-time average cardiac interval to be synchronized with the first vibration stimulus;

(II-1) on condition that the first vibration stimulus, which has a first average cardiac interval corresponding to the first reference heart rate information as the first period, is applied to the user, configuring a heart rate measurement unit to obtain the user's real-time heart rate information and obtaining the user's cardiac change rate by referring to the real-time heart rate information;

(II-2) maintaining a state that the first vibration stimulus with the first period is applied to the user during a time when an active state value of a parasympathetic nerve at the user's cardiac change rate converges to a predetermined first reference value;

(II-3) on condition that the active state value of the parasympathetic nerve is less than the predetermined first reference value or does not converge to the predetermined first reference value, the processor further performs a process of (II-3) gradually changing a period of the first vibration stimulus from an n-th period, corresponding to the real-time heart rate information, to the first period, and supporting the first vibration stimulus with an (n-k)-th period, which is each changed period, to be applied to the user, to thereby allow the real-time average cardiac interval to be gradually synchronized with the first vibration stimulus;

(II-4) maintaining a state that the first vibration stimulus with the first period is applied to the user during a time when an active state value of a sympathetic nerve at the user's cardiac change rate converges to a predetermined second third reference value, on condition that the active state value of the sympathetic nerve is less than the predetermined second reference value or does not converge to the predetermined second reference value, the processor further performs a process of (II-5) gradually changing the period of the first vibration stimulus from the n-th period, corresponding to the real-time heart rate information, to the first period, and supporting the first vibration stimulus with the (n-k)-th period, which is each changed period, to be applied to the user, to thereby allow the real-time average cardiac interval to be gradually synchronized with the first vibration stimulus wherein the predetermined first reference value is a maximum active state value of the parasympathetic nerve and the predetermined second reference value is a maximum active state value of the sympathetic nerve, both of which are obtained by the cardiac change rate in the specific active state of the user's autonomic nervous system.

12. The inducing device of claim 11, wherein, at the process of (II), the processor sets the first period of the first vibration stimulus to the first average cardiac interval corresponding to the first reference heart rate information.

13. The inducing device of claim 11, wherein, at the step of (II-2), the processor maintains a state of allowing the first vibration stimulus with the first period to be applied to the user during a time when the active state value of the parasympathetic nerve at the user's cardiac change rate converges to the predetermined first reference value and, at the same time, the active state value of the sympathetic nerve at the user's cardiac change rate converges to the predetermined third reference value, wherein the predetermined third reference value is a minimum active state value of the sympathetic nerve, which is obtained by the cardiac change rate in the specific active state of the user's autonomic nervous system.

14. The inducing device of claim 11, wherein, at the process of (II-3), on condition that (i) the active state value of the parasympathetic nerve is less than the predetermined first reference value or does not converge to the predetermined first reference value, and, at the same time, (ii) the active state value of the sympathetic nerve at the user's cardiac change rate exceeds a predetermined third reference value or does not converge to the predetermined third reference value, the processor gradually changes the period of the first vibration stimulus from the n-th period, corresponding to the real-time heart rate information, to the first period, and supports the first vibration stimulus with the (n-k)-th period, which is each changed period, to be applied to the user, to thereby allow the real-time average cardiac interval to be gradually synchronized with the first vibration stimulus, wherein the third reference value is a minimum active state value of the sympathetic nerve, which is obtained by the cardiac change rate in the specific active state of the user's autonomic nervous system.

15. The inducing device of claim 11, wherein, at the process of (II), the processor performs a process of:

(II-6) obtaining the user's real-time heart rate information, supporting the first vibration stimulus with the (n-k)-th period representing the period from the n-th period, which is the user's real-time average cardiac interval corresponding to the real-time heart rate information, to the first period, to be gradually applied to the user, obtaining the user's cardiac change rate by referring to the user's gradually obtained real-time heart rate information, and maintaining a state that the first vibration stimulus with the first period is applied to the user until the active state value of the parasympathetic nerve at the user's cardiac change rate reaches the predetermined first reference value, wherein the predetermined first reference value is the maximum active state value of the parasympathetic nerve, which is obtained by the cardiac change rate in the specific active state of the user's autonomic nervous system.

16. The inducing device of claim 15, wherein, at the process of (II-6), the processor maintains a state of allowing the first vibration stimulus to be applied to the user until the active state value of the parasympathetic nerve at the user's cardiac change rate reaches the predetermined first reference value, and the active state value of the sympathetic nerve at the user's cardiac change rate reaches a predetermined third reference value, wherein the predetermined third reference value is a minimum active state value of the sympathetic nerve, which is obtained by the cardiac change rate in the specific active state of the user's autonomic nervous system.

17. The inducing device of claim 11, wherein, at the process of (II), the processor performs a process of:

(II-7) obtaining the user's real-time heart rate information, supporting the first vibration stimulus with the (n-k)-th period representing the period from the n-th period, which is the user's real-time average cardiac interval corresponding to the real-time heart rate information, to the first period, to be gradually applied to the user, obtaining the user's cardiac change rate by referring to the user's gradually obtained real-time heart rate information, and maintaining a state that the first vibration stimulus with the first period is applied to the user until the active state value of the sympathetic nerve at the user's cardiac change rate reaches the predetermined second reference value, wherein the predetermined second reference value is the maximum active state value of the sympathetic nerve, which is obtained by the cardiac change rate in the specific active state of the user's autonomic nervous system.

18. The inducing device of claim 11, wherein, at the process of (II), the processor performs a process of:
   (II-8) obtaining the user's real-time heart rate information, obtaining the user's cardiac change rate by referring to the real-time heart rate information, and supporting a second vibration stimulus, which is generated by changing the first vibration stimulus, to be applied to the user if the active state value of the parasympathetic nerve at the user's cardiac change rate does not converge to the predetermined first reference value, wherein the predetermined first reference value is the maximum active state value of the parasympathetic nerve, which is obtained by the cardiac change rate in the specific active state of the user's autonomic nervous system.

19. The inducing device of claim 11, wherein, at the process of (II), the processor performs a process of:
   (II-9) obtaining the user's real-time heart rate information, obtaining the user's cardiac change rate by referring to the real-time heart rate information, and supporting a third vibration stimulus, which is generated by changing the first vibration stimulus, to be applied to the user if the active state value of the sympathetic nerve at the user's cardiac change rate does not converge to the predetermined second reference value, wherein the predetermined second reference value is the maximum active state value of the sympathetic nerve, which is obtained by the cardiac change rate in the specific active state of the user's autonomic nervous system.

20. The inducing device of claim 11, wherein the first vibration stimulus is a non-recognized vibration stimulus which is not recognized by the user.

* * * * *